United States Patent [19]
Bullara et al.

[11] Patent Number: 5,993,453
[45] Date of Patent: Nov. 30, 1999

[54] CONTROLLED-DEPTH BONE CUTTER

[75] Inventors: Leo A. Bullara, Glendora; Stephen H. Waldron, Camarillo, both of Calif.

[73] Assignee: Huntington Medical Research Institutes, Pasadena, Calif.

[21] Appl. No.: 09/173,231

[22] Filed: Oct. 15, 1998

Related U.S. Application Data

[60] Provisional application No. 60/062,041, Oct. 15, 1997.

[51] Int. Cl.⁶ .................................................. A61B 17/14
[52] U.S. Cl. .................................. 606/79; 606/82; 606/86
[58] Field of Search ................................. 606/79, 80, 82, 606/86, 96

[56] References Cited

U.S. PATENT DOCUMENTS 3,678,934  7/1972  Warfield et al. ........................ 128/317
5,782,836  7/1998  Umber et al. ............................ 606/79
5,893,851  4/1999  Umber et al. ............................ 606/80
5,910,121  6/1999  Paolo et al. ............................. 606/79

*Primary Examiner*—Michael Buiz
*Assistant Examiner*—Daphna Shai
*Attorney, Agent, or Firm*—Christie, Parker & Hale, LLP

[57] ABSTRACT

A surgical tool for controlling the depth of penetration of a cutter into bone. The tool has a tubular housing with three legs extending therefrom to provide a tripod-like support when positioned against the bone surface. A penetration-depth adjustment ring or sleeve is rotatable on the tubular housing, preferably in click-stop detented intervals, to establish a desired penetration depth for the cutter.

4 Claims, 3 Drawing Sheets

CONTROLLED-DEPTH BONE CUTTER

CROSS REFERENCE TO RELATED APPLICATION

This application claims the benefit of U.S. Provisional Application No. 60/062,041 filed Oct. 15, 1997.

BACKGROUND OF THE INVENTION

This invention relates to a cutting tool enabling a neurosurgeon or orthopedic surgeon to shape, shave or bore bone. The tool is useful, for example, in forming a precisely contoured depression in bone to receive a transcutaneous connector used in a nerve stimulation system. The connector typically has an undersurface of known curvature, and which is coated with tiny titanium beads which encourage bone ingrowth after implantation. To achieve such ingrowth, it is important that the bone surface in which the connector is seated be contoured to exactly match the connector contour so the facing surfaces are in intimate contact. The tool enables precise control of cutting depth, and is equally useful in the boring of precise holes in bone with control over both hole diameter and depth.

Controlled-depth cutters have been in use in industry for many years for forming countersink surfaces and the like, but these products are intended for use against a flat metal surface, and are typically adjusted by trial and error after making several experimental cuts. The tool of this invention has three extended and pointed-tip legs which enable stable three-point positioning against a curved bone surface, and which provide visibility for the surgeon of the surface being cut. The tool can also be preset to a predetermined cutting depth with a click-stop adjustment which is easily manipulated in a surgical environment.

SUMMARY OF THE INVENTION

Figure 1:
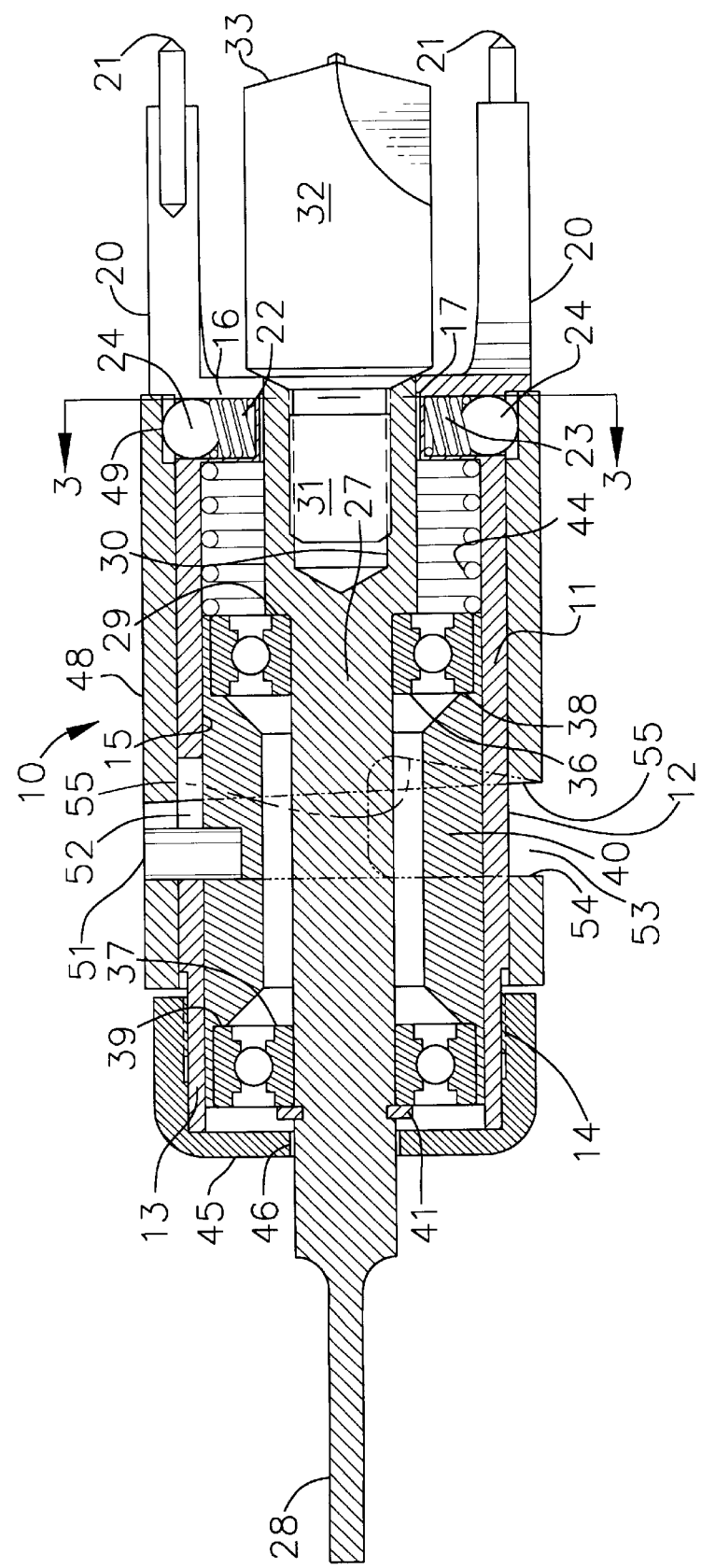
FIG. 1 is a sectional elevation of the tool.

The surgical tool of this invention includes a tubular housing with three forwardly extending and circumferentially spaced support legs for stable positioning against a bone surface to be cut. A drive shaft extends centrally through the tubular housing, and is supported by bearings mounted in a bearing support tube making a slip fit within the housing. A cutter is engaged with a forward end of the drive shaft, and the cutter, drive shaft and support tube are urged by a spring into a retracted position placing the cutter out of contact with the bone. Forward movement of the drive shaft during cutter rotation by a drive means is adjustably limited by a radially extending pin secured to the support tube and extending into a variable-width part-circumferential slot extending through an adjustment sleeve rotatably fitted over the tubular housing.

DESCRIPTION OF THE PREFERRED EMBODIMENT

Referring to the drawings, a bone cutting tool 10 has an inner tubular housing 11 with a cylindrical outer surface 12. A rear end 13 of the housing is slightly reduced in diameter, and threads 14 are formed on its outer surface. The inner surface of the housing is a smooth cylindrical bore 15 extending from the housing rear end to an inwardly extending front ring 16 with a central circular opening 17.

Three support legs 20 are circumferentially spaced 120-degrees apart, and extend forwardly from front ring 16. Each leg 20 terminates in a sharpened-tip pin 21 seated in and extending from the leg, the tips being pressed against the bone being contoured to prevent unwanted lateral or rotational movement. A pair of radially inwardly extending detent-ball sockets 22 are formed in front ring 16 at a 180-degree spacing, and a compression spring 23 and detent ball 24 are seated in each of the sockets.

A drive shaft 27 extends centrally through housing 11, and has a rearwardly extended end 28 of reduced diameter for engagement with the chuck of a drill motor (not shown) or similar drive means. A forward portion of the shaft is enlarged in diameter to form a rearwardly facing annular shoulder 29. The forward end of the shaft has an internally threaded bore 30 to receive an externally threaded shank 31 of an interchangeable cutter 32 having cutting surfaces 33. The cutting surfaces may be convex, concave, or flat, depending on the desired shape of the bone depression to be machined.

Drive shaft 27 is supported within housing 11 by front and rear ball bearings 36 and 37, the outer parts of which are fitted in mating annular seats 38 and 39 at opposite ends of a bearing support tube 40. The support tube makes a close slip fit within bore 15 of the housing, and the shaft and support tube are axially movable with respect to the housing. The front of front bearing 36 is held captive in seat 38 by annular shoulder 29 of the drive shaft, and a snap ring 41 is fitted in a groove of the drive shaft to restrain rearward movement of rear bearing 37 out of seat 39.

A compression spring 44 is fitted within bore 15 of the housing between the front end of bearing support tube 40 and the rear surface of front ring 16. The rear end of the tool is closed by a cover cap 45 which is threaded onto threads 14 of the housing. Cap 45 has a central clearance opening 46 through which the rear end of the drive shaft extends.

Figure 3:
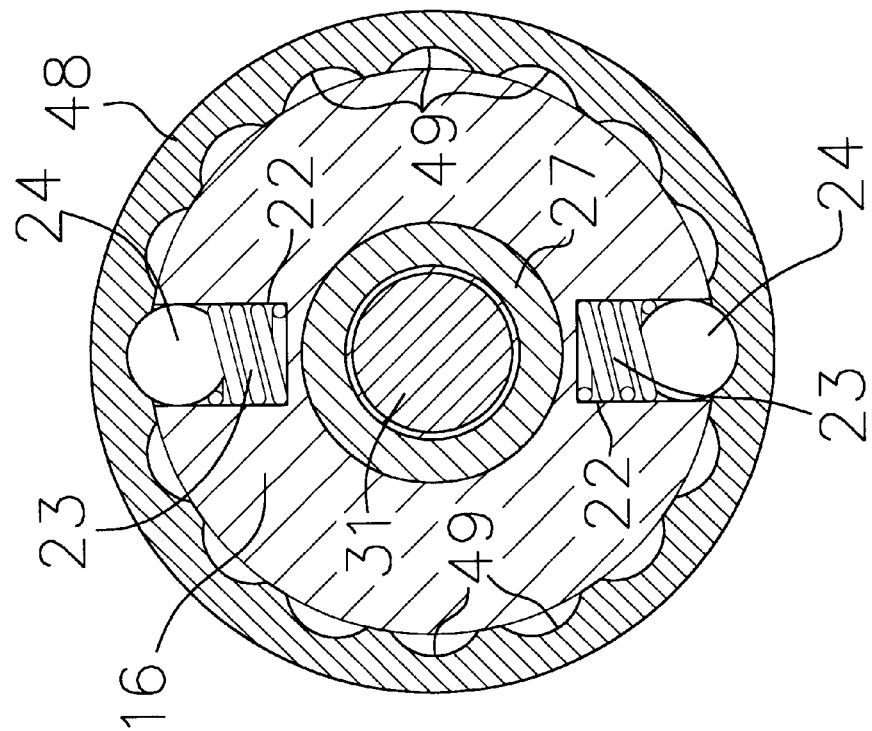
FIG. 3 is an end sectional view on line 3—3 of FIG. 1.
Figure 2:
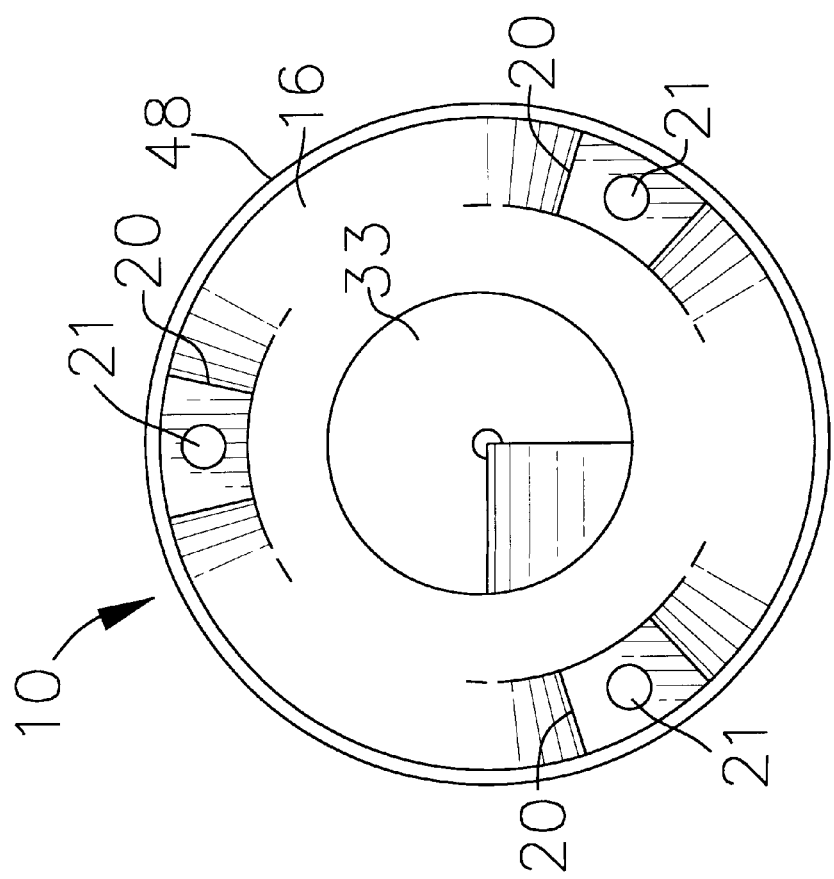
FIG. 2 is an end view of the tool taken from the right side.

A generally cylindrical outer adjustment sleeve 48 is fitted on outer surface 12 of the housing, and is rotatable with respect to the housing. An inner surface of the front end of sleeve 48 defines a plurality of radially extending and circumferentially spaced detent seats 49 in axial alignment with detent ball sockets 22 as best seen in FIG. 3. Balls 24 in the detent sockets are urged into opposed seats 49 by springs 23.

The extent of axial movement of the drive shaft and cutter is controlled by a pin 51 which is rigidly secured to bearing support tube 40. The pin extends radially outwardly through a longitudinally elongated slot 52 in the sidewall of housing 11, and into a circumferential slot 53 which extends through and partially around adjustment sleeve 48.

A rear surface 54 of slot 53 is flat, and spring 44 urges pin 51 against the rear surface to establish the shaft and cutter in a retracted position as shown in FIG. 1. A front surface 55 of slot 53 diverges from flat rear surface 54 to provide a variable slot width as the slot extends circumferentially.

Adjustment sleeve 48 is rotated about housing 11 to set a desired width of slot 53 in alignment with pin 51, and thus to adjust the extent to which the drive shaft and cutter can be advanced. In a typical configuration, the slot and detent seats are configured to provide an axial adjustment in steps of about 0.2 millimeters as the sleeve is moved from one detent-seated position to the next such position.

Figure 4:
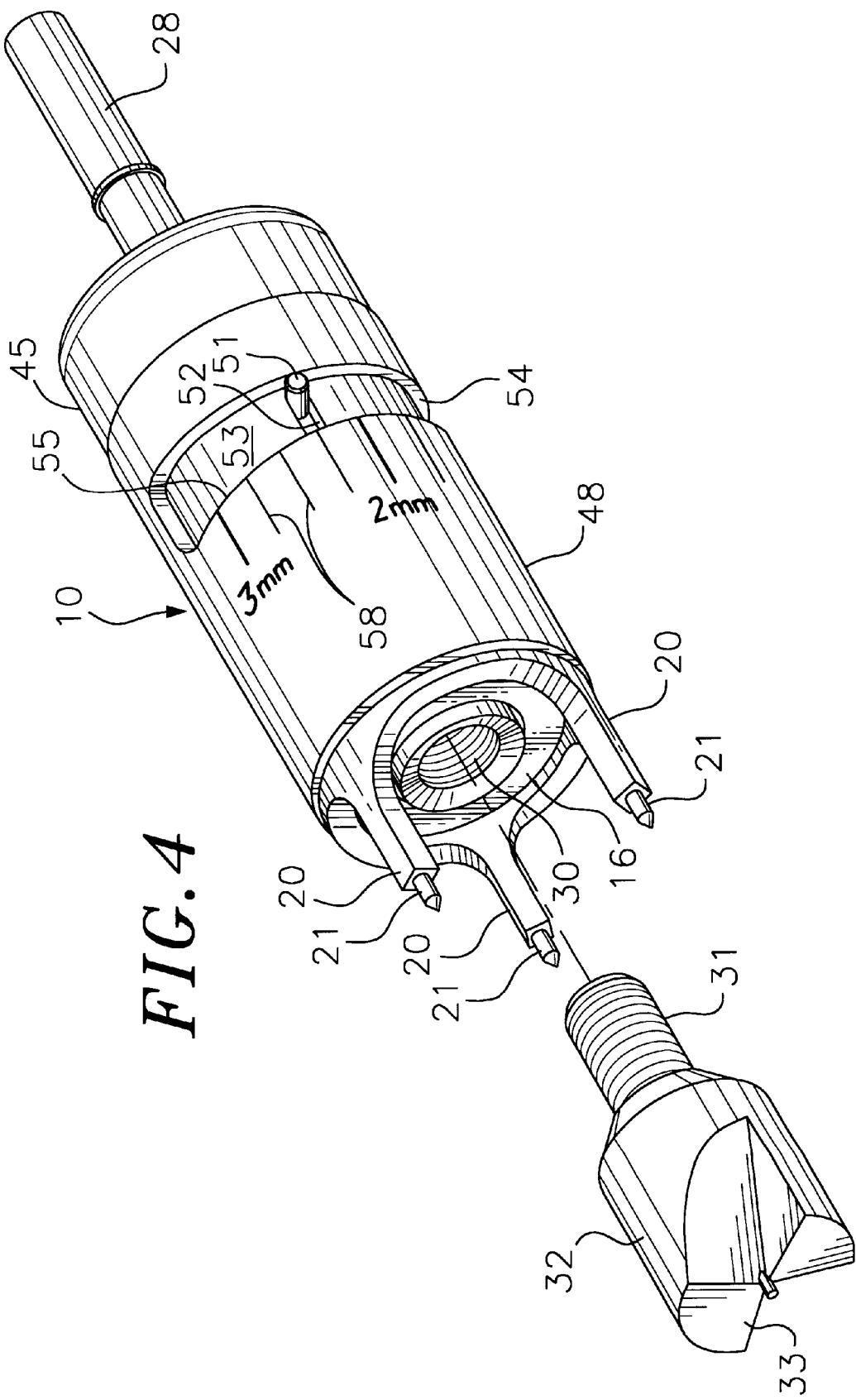
FIG. 4 is a perspective view of the tool and an associated cutter.

In the tool shown in the drawing the range of axial movement is about 0.25 to 3 or 4 millimeters, but this range is easily varied by reconfiguring the shape of circumferential slot 53, and a typical range is 1 to 6 millimeters. Preferably, a depth scale 58 (FIG. 4) is marked around the outer surface of sleeve 48 adjacent the slot 53 to enable immediate reading (with respect to the selected position of pin 51)of the permitted axial movement.

In use, a cutter of the desired shape is threaded into the drive shaft, and a conventional rotational drive means (800 rpm is a typical speed) is secured to shaft rear end 28. The tool is then positioned over an exposed bone surface to be cut, with support-leg tips 21 pressed against the bone to provide a firm tripod-like support. The rotation means is then activated, and the drive shaft pressed forward against compression spring 44 to contour and cut the bone to a desired depth as set by the relative rotational click-stop adjustment of sleeve 48 and pin 51 which can be conveniently varied during a surgical procedure.

The tool is preferably made of stainless steel so it can be sterilized by autoclaving or similar procedures.

What is claimed is:

1. A surgical tool for cutting a predetermined contour of predetermined depth in bone, comprising:

a tubular housing having front and rear ends, the housing having three circumferentially spaced support legs extending from the front end, the support legs having tips for contacting the bone;

a drive shaft having a rear end configured for attachment to a rotation drive means, and a front end configured to receive a bone cutter;

a bearing support tube making a rotatable slip fit within the housing, and including bearings for rotatably supporting the drive shaft as centrally positioned within the housing and support tube, the drive shaft being axially fixed to the support tube;

a resilient means positioned between the housing and support tube for urging the support tube and drive shaft to a normally retracted position in which the cutter is retracted from a plane defined by the support-leg tips;

an adjustment sleeve fitted over and rotatable on the tubular housing; and means coupling the adjustment sleeve and support tube for adjustably limiting the extent of axial movement of the support tube and drive shaft when axially forced against the resilient means.

2. The tool defined in claim 1, and further including detent means positioned between the tubular housing and adjustment sleeve to define a plurality of stable rotational positions of the sleeve on the housing corresponding to specific axial movements of the support tube as set by the adjustment sleeve.

3. The tool defined in claim 2, and further comprising a scale on the adjustment sleeve to display axial-movement freedom of the support tube for various rotational positions of the sleeve.

4. The tool defined in claim 3 wherein the coupling means comprises a circumferential and variable-width slot extending through and part way around the adjustment sleeve, and a radially extending pin secured to the support tube into the adjustment-sleeve slot, the tubular housing having a longitudinal slot providing clearance for the pin.

* * * * *